United States Patent [19]

Slavin et al.

[11] Patent Number: 5,594,005
[45] Date of Patent: Jan. 14, 1997

[54] USE OF QUINOLINE-3-CARBOXAMIDE COMPOUNDS FOR TREATMENT OF DIABETES

[75] Inventors: Shimon Slavin; Lola Weiss; David Gross, all of Jerusalem, Israel

[73] Assignee: Pharmacia AB, Stockholm, Sweden

[21] Appl. No.: 313,302

[22] PCT Filed: Mar. 31, 1993

[86] PCT No.: PCT/SE93/00272

§ 371 Date: Dec. 23, 1994

§ 102(e) Date: Dec. 23, 1994

[87] PCT Pub. No.: WO93/19756

PCT Pub. Date: Oct. 14, 1993

[30] Foreign Application Priority Data

Apr. 6, 1992 [SE] Sweden ................................ 9201076

[51] Int. Cl.$^6$ ...................................... A61K 31/47
[52] U.S. Cl. .................. 514/311; 514/312; 514/866; 514/884
[58] Field of Search .................. 514/311, 312, 514/866, 884

[56] References Cited

U.S. PATENT DOCUMENTS

| | | | |
|---|---|---|---|
| 3,960,868 | 6/1976 | Ferrini et al. | 546/156 |
| 4,107,310 | 8/1978 | Allais et al. | 514/312 |
| 4,542,139 | 9/1985 | Hitzel et al. | 514/312 |
| 4,547,511 | 10/1985 | Eriksoo et al. | 514/312 |
| 4,738,971 | 4/1988 | Eriksoo et al. | 514/312 |
| 5,310,913 | 5/1994 | Gunnarsson et al. | 546/155 |

OTHER PUBLICATIONS

Woods, Pathogenesis of Systemic Lupus Erythematosus 60: 999–1016 (1986).

*Primary Examiner*—Kevin E. Weddington
*Attorney, Agent, or Firm*—Birch, Stewart, Kolasch & Birch, LLP

[57] ABSTRACT

Quinoline-3-carboxamide compounds of formula (I) are effective in preventing, treating or ameliorating Type I diabetes.

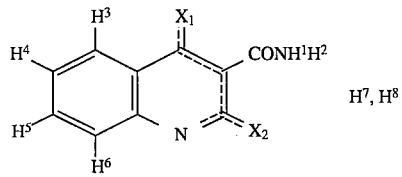

wherein ----- represents two conjugated double bonds between the atoms comprised by the dashed line, $X_1$ and $X_2$ are independently selected from an oxygen atom or $NH^9$, $H^{1-9}$ independently represent a hydrogen atom or a substituent, wherein $H^7$ and $H^8$ are attached to different atoms selected from $X_1$, $X_2$ and the ring nitrogen atom of the quinoline ring. In particular, $X_1$ and $X_2$ being bound by a single bond to the ring when $H^7$ or $H^8$ is bonded thereto and by a double bond when $H^7$ or $H^8$ is not bonded thereto.

9 Claims, No Drawings

USE OF QUINOLINE-3-CARBOXAMIDE COMPOUNDS FOR TREATMENT OF DIABETES

This application is a 371 of PCT/SE 93/00272 filed Mar. 31, 1993.

GENERAL BACKGROUND

Diabetes mellitus is a disease characterized by physiologic and anatomic abnormalities in many organs, due to vascular abnormalities. However, the most prominent feature of the disease is disturbed glucose metabolism, resulting in hyperglycemia. Diabetes mellitus is usually divided into two major categories: insulin-dependent diabetes mellitus (Type I diabetes), which usually develops in childhood or adolescence and these patients are prone to ketosis and acidosis. The second category of patients (Type II diabetes) are not insulin dependent and usually manage with diet and oral hypoglycemic therapy. The annual incidence of Type I diabetes ranges from 10 cases/100.000 persons for non-white males to 16 cases/100.000 persons for white males in the United States, with equal incidence between males and females. The prevalence of Type I diabetes for all ages in the United States population is 160 cases/100.000 persons, with a slightly earlier onset for females with peak age of onset at 10–12 years than for males with peak age of onset at 18 years. Genetic background plays a major role in the development of the disease, with 40% concordance for Type I diabetes exhibited by identical twins and increased incidence among family members. Genes associated with increased susceptability to Type I diabetes reside near the major histocompatibility complex on chromosome 6, with more than 90% of persons with Type I diabetes featuring DR3 or DR4 haplotypes or both. Likewise, siblings sharing DR3 or DR4 haplotypes from both parents more often than random develop Type I diabetes (1).

The onset of symptoms in Type I diabetes is usually acute and frequently follows an antecedant vital infection which might be the trigger to a process leading to destruction of the beta cells secondary to autoimmune insulitis. When beta cell destruction reaches the critical point, the patient's reduced insulin levels lead to hyperglycemia with the typical symptomatology of Type I diabetes. At diagnosis approximately 70% of patients with Type I diabetes have antibodies to islet cell cytoplasm i.e. antigens or to components of the islet cell surface. Approximately 15% of patients with Type I diabetes may also show other autoimmune features, such as hypothyroidism, Graves' disease, Addison's disease, myasthenia gravis and pernicious anemia (2). Autopsies of cases with Type I diabetes show a typical lymphocytic infiltration in the pancreatic islets (3).

Treatment of Type I diabetes at present is not satisfactory and the disease leads to serious life-threatening complications that can be only partly overcome with adequate control of insulin levels, which is usually difficult to accomplish in patients with juvenile onset. In addition to the acute diabetic syndrome, chronic manifestations lead to severe arteriosclerosis with microadenopathy affecting the eye with possible early blindness. One in 20 of all Type I diabetes patients becomes blind; about 40% of Type I diabetes develop renal failure, resulting in chronic hemodialisis and/or the need for renal transplantation (4–7). Severe neuropathic changes are also typical for Type I diabetes with many functional disorders associated with sensory, sympathetic and para-sympathetic nerves. Cranial nerve, as well as peripheral nerve, may be involved. Treatment of neuropathy remains unsatisfactory, despite normal control of glucose levels with adequate insulin therapy.

Strokes are twice as frequent, myocardial infarctions are 2–5 times as frequent and cardiovascular accidents are 5–10 times more frequent in patients with Type I diabetes than among non-diabetic counterparts. The prognosis of patients with Type I diabetes who survive acute myocardial infarction is 3 times more grave compared to non-diabetics who survive acute infarction and the same is true for other vascular complications. Severe and uncontrollable arterosclerosis may also be associated with a variety of etiologies involving abnormalities in platelets, clotting factors and lipid carriers, such as HGL levels, as well as uncontrolled diabetes (1).

In view of the autoimmune nature of the disease, cyclosporine A has been suggested as a possible treatment of choice soon after the clinical manifestations of Type I diabetes with some encouraging results (8). Although complete and partial remission have been reported, randomized double-blind clinical trials are needed to assess the long-term effectiveness and safety of cyclosporine and other immunosuppressive modalities early in the course of IDDM.

The invention is further illustrated by the following experiments:

In order to study the effect of treatment regimens in connection with diabetes the experimental model with non-obese diabetic (NOD) mice has been commonly used. See the experimental part. Drugs counteracting lymphocytic infiltration of the pancreatic islets with subsequent degenerative changes, overt diabetes, manifesting hyperglycaemia, glycosuria, ketosis and weight loss, with an absolute requirement for insulin after the development of hyperglycaemia, are here and further on in connection with the invention defined as anti-diabetic drugs.

Quinoline-3-carboxamide compounds have been suggested as pharmaceuticals. The compounds have comprised the structure given in formula I below, optionally with substituents for the hydrogen atoms shown ($H^{1-9}$, where $H^9$ is part of $X_1$ or $X_2$ as shown in (b) below) and, where appropriate, salts of the compounds:

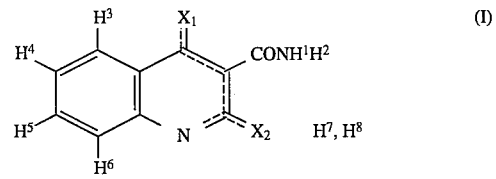

(I)

This formula is a collective formula for the tautomeric structures II–IV.

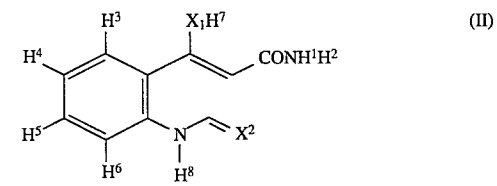

(II)

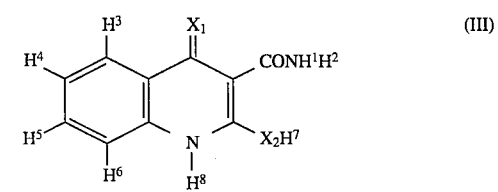

(III)

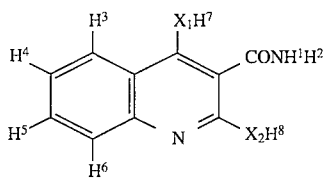

In formula I–IV:

(a) ----- represents that there are two conjugated double bonds between the atoms comprised by the dashed line (only formula I).

(b) $X_1$ and $X_2$ are separately selected from an oxygen atom or an $NH^9$ group that possibly is substituted, said $X_1$ and $X_2$ being bound by a single bond to the ring when attached to $H^7$ or $H^8$ and by a double bond when not bound to $H^7$ or $H^8$.

(c) $H^{1-9}$ are hydrogens, with the provision that $H^9$ is only present when at least one of $X_1$ and $X_2$ is the $NH^9$ group.

(d) $H^7$ and $H^8$ are hydrogens that are attached to different atoms selected among $X_1$, $X_2$ and the nitrogen atom in the quinoline ring said $X_1$ and $X_2$ being bound by a single bond to the ring when attached to $H^7$ or $H^8$ and by a double bond when not bound to $H^7$ or $H^8$.

The substituents that are to replace $H^{1-9}$ may, according to the prior art, comprise any substituent that gives compounds that can be isolated. See for instance Indian Journal of Chemistry Vol 17B (1979) 488–90 (anti-inflammatory properties), U.S. Pat. No. 3,960,868 (=GB 1,467,061, analgesic, anticonceptive, anti-inflammatory and anti-allergic properties), U.S. Pat. Nos. 4,547,511 and 4,738,971 (enhancing cell-mediated immunity), WO 9015052 (=U.S. Ser. No. 651,234, filed May 31, 1990) immunomodulator), U.S. Pat. No. 4,107,310 (analgetics) and JP 68023948 (bacteriocides). U.S. patents and patent applications given above are hereby incorporated by reference. In general it can be stated that many of the compounds comprising structure I are classified as immune modulators with individual effects spanning the spectra from suppression to stimulation of the immune system. The specific effect achieved depends on the substituents.

One of the most important compounds with formula I are the 1,2-dihydro-hydroxyquinoline-3-carboxamides, particularly N-phenyl-N-methyl-1,2-dihydro-4-hydroxy-1-methyl-2-oxo-quinoline-3-carboxamide (Linomide®), i.e. structures I and II with a substituent for $H^1$ that equals phenyl, for $H^2$ that equals methyl, for $H^8$ that equals methyl (attached to the nitrogen atom of the quinoline ring), with no substituents for $H^{3-7}$, with $H^7$ attached to $X_1$, and with each of $X_1$ and $X_2$ equaling an oxygen atom. The compound has double bonds between positions 3 and 4 and between position 2 and $X_2$.

The scientific experimentation with Linomide® has shown that Linomide has multiple immunological activities. It has thus been found that Linomide® increases the proliferative response to T and B cell mitogens (8), enhances antibody production (9) and augments NK cell activity (10, 11). Moreover, its immunostimulating and immunoregulating properties may be useful in the treatment of tumors (12) and systemic lupus erythematosis (13, 14) as suggested in U.S. Pat. Nos. 4,547,511 and 4,738,971.

OBJECTIVES OF THE INVENTION

One major objective of the invention is to provide a method for the treatment of Type I diabetes mellitus.

A second major objective is to provide drugs to be used for the manufacture of pharmaceutical compositions intended for the treatment of the conditions given the preceding paragraph.

Other objectives are to provide methods, drugs and pharmaceutical compositions that in connection with the conditions given above decrease lymphocytic infiltration of the pancreatic islets, hyperglycaemia, glycosuria, ketosis, weight loss or requirement for insulin.

In the invention mammalian species that can develop Type I diabetes, are treated, in particular humans.

THE INVENTION

Based on our study of the pronounced immune stimulator Linomide® in the NOD mice model, we have found that, in contrast to earlier treatment strategies based on non-specific immune suppression, Linomide® exerts an extremely efficient antidiabetic effect. By studying other compounds comprising structure I further drug candidates showing similar effects will be found.

Thus the present invention concerns a method for the treatment of diabetes as defined above under the heading "Objectives of the invention". The method means administration of a therapeutically effective mount of an antidiabetic compound comprising structure I. The inventive method includes prophylactic treatment. The invention also comprise the use of the compounds for the manufacture of a pharmaceutical composition to be employed in the method.

For the time being it is believed that the most preferred compounds can be found among those described in U.S. Pat. Nos. 4,738,971 and 4,547,511. In particular combinations of substituents may be selected from:

(i) $H^8$ is replaced by a group selected from lower alkyls (containing 1–8 carbon atoms) and bound to the nitrogen atom of the quinoline ring ($H^8$=lower alkyl);

(ii) $X_1$ is oxygen to which $H^7$ is bound (=—OH group);

(iii) $X_2$ is oxygen which is connected to the quinoline ring by a double bond (since $X_2$ is oxygen $H^9$ is not present);

(IV) none of the $H^{1-6}$ is replaced by a substituent ($H^{1-6}$= hydrogens); and (v) $H^1$ is replaced by an aryl, in particular a phenyl group ($H^1$=aryl in particular phenyl) and/or $H^2$ by a lower alkyl (containing 1–8 carbon atoms).

The particularly preferred compound is Linomide®, or a physiologically and pharmaceutically acceptable salt thereof that is therapeutically active, e.g. an Na- or Ca-salt.

By the term effective amount is meant that the amount shall ameliorate the diabetic status of the patients with respect to the effects given above.

The administration route is primarily oral, but this does not exclude other routes such as parenteral, intraperitoneal, injection, infusion, rectal etc. administration.

The compositions referred to by the invention may contain the active compound as such or, where appropriate in form of a salt of a pharmaceutically acceptable cation or an/on as known in the art. A conceivable dosage range from 0.1–100 mg a day, depending on the specific condition to be treated, the age and weight of the specific patient, and the patient's specific response to the medication. Normally the effective dosage amount is from 0.01–10, preferably 0.05–1 mg/kg body weight.

Formulations that may be used are powder, syrups, suppositories, ointments, solutions, pals, capsules, pellets etc.

with or without, but preferably with pharmaceutically acceptable carriers. See further U.S. Pat. Nos. 4,738,971 and 4,547,511 that are incorporated by reference.

EXPERIMENTAL MODEL

The non-obese diabetic (NOD) mice were discovered and inbred in the 70s and since then have served as an outstanding model for understanding the processes and mechanisms leading to the destruction of islet beta cells in Type I diabetes and made it possible to test several preventive measures. NOD mice develop early lymphocytic infiltration of the islets of the pancreas, with degenerative changes starting at the age of 3–4 weeks. The insulitis leads to overt diabetes at 13–30 weeks, manifesting severe hyperglycemia, glycosuria, ketosis, and weight loss, with an absolute requirement for insulin after the development of hyperglycemia. Insulitis is more prevalent among females (at 30 weeks, incidence of females to males 85% to 20%) (15). Whereas insulitis is apparent both in males and females, overt diabetes has a female/male ratio of 85% to 15%, which indicates the role of additional factors such as hormones in the development of the diabetes syndrome (15).

Diabetes in NOD mice is clearly immune-mediated and T-cell deficient mice do not develop the full manifestations of the disease (16–18). Hence, immunosuppressive modalities, including cyclosporine A, FK-506, anti-thymocyte globulin, monoclonal anti-Thy-1 or anti-CD4 antibodies, as well as irradiation and bone marrow transplantation, may prevent or ameliorate, at least transiently, both the hyperglycemia and insulitis (19–25).

THE EFFECT OF LINOMIDE ON THE DEVELOPMENT OF DIABETES IN NOD MICE

Materials and Methods

Mice. Female NOD mice purchased from Bomholtgard Breeding and Research Centre Ltd., Denmark, were used for all experiments. These animals start developing insulitis at 3–5 weeks of age, frank diabetes 55% at 26 weeks, 65% at 28 weeks, at ambient temperature of 21°±8° C. The onset of diabetes was determined on the basis of appearance of glycosuria on two consecutive determinations checked biweekly with Labstix. Subsequently, glucose levels were determined in the blood before and after intraperitoneal glucose tolerance test. Animals were weighed biweekly.

Glucose tolerance test (GTT). GTT was performed by intraperitoneal injection of 1 g/kg body weight glucose and determination of glucose blood levels at base line and at 60' following injection of glucose.

Histopathological evaluation. Animals were sacrificed at 12 weeks of age, approximately 8 weeks after initiation of the experiment, and histopathology of the pancreas was evaluated in treated animals in comparison with controls on a blind basis. Pathology of other organs was also assessed to test for possible drug-related toxicity.

Linomide administration. Linomide (Kabi Pharmacia Therapeutics AB, Helsingborg, Sweden) was dissolved in acidified drinking tap water at a concentration of 0.5–2.5 mg/ml. It only slightly influenced (reduced) water consumption, especially at the high doses used. At the lower dose used, each mouse received an estimated quantity of 1.5–2.5 mg/kg/day (60–100 mg/kg). Linomide administration was initiated at 3–5 weeks of age. A fresh dilution of the drug was prepared every 10 days. Control animals received regular acidified tap water only.

Clinical evaluation of diabetes and insulitis. Experimental mice were divided into two groups and placed on Linomide therapy, starting at 3–5 weeks of age. Urine glucose, body weight and fluid intake were determined regularly on a biweekly basis. Animals were sacrificed for histopathological evaluation of the pancreas and other organs at 12 weeks of age and GTT was determined at 16 weeks of age. Survival was determined on a daily basis.

RESULTS

Onset of glucosuria. Glucosuria appeared only in controls and none of the mace treated with Linomide showed any evidence of glucosuria by Labstix, as follows:

Experiment 1

Animals 40 weeks old, controls 5/9 with glucosuria, Linomide (0.5 mg/ml) 0/9 with glucosuria.

Experiment 2

Animals 40 weeks old, controls 4/9 with glucosuria, Linomide (0,5 mg/ml) 0/9 with glucosuria.

Basic blood levels and glucose tolerance test. Results of intraperitoneal GTT, as shown in FIG. 1: Typical diabetic pattern was noted in untreated controls with elevated basic blood sugar levels in the majority of mice and increased glucose levels following loading of glucose. In contrast, normal blood sugar levels were noted in NOD mice treated with Linomide and the normal GTT test was comparable to the GTT levels observed following GTT in normal BALB/c recipients.

Pathology. Pathological examination of pancreata (3 animals/group/experiment) were done on a double blind basis (neither the pathologist, Prof. E. Rosemann, nor the observer knew the code of the slides that were marked with numbers). Typical features of insulitis, including heavy mononuclear cell infiltration in the beta islets, were noted in all untreated NOD mice. No evidence of insulitis was noted in any of the mice that were treated with Linomide. The correlation was absolute: None of the treated animals featured insulitis and, conversely, typical insulitis was observed among all untreated recipients.

Body weight. Untreated controls continued to develop weight loss in parallel with the onset of oven glucosuria. In contrast, Linomide treated NOD mice started to gain weight, as shown in FIG. 2.

Survival. All treated mice from experiments 1 and 2 continue to survive, with the exception of one animal, whereas death was already noted among untreated controls, as can be seen in FIG. 3.

SUMMARY

Results of our ongoing experiments show that Linomide can markedly ameliorate autoimmune insulitis with maintenance of normal glucose metabolism following oral administration. Successfully treated mice showed no clinical evidence of disease in absence of glucosuria, normal blood glucose tolerance, no pathological signs of autoimmune insulitis and no evidence of drug toxicity. In contrast, untreated controls developed typical parameters of diabetes mellitus, including glucosuria, hyperglycemia, weight loss and death, with typical mononuclear cell infiltration in beta cells of the pancreas whenever examined.

REFERENCES

1. Cahill G. F. et al. In Scientific American Medicine, vol. 2: Diabetes mellitus, pp 1–20
2. Powers A. C. et al. Ann Rev Med 1985;36:533

3. Lernmark A. Diabetologia 1985;28:195
4. Ganda O. P. Diabetes 1980;29:931
5. Colwell J. A. et al. Diabetes Care 1981;4:121
6. Lopes-Virella M. F. et al. Diabetologia 1981;21:216
7. Andersen A. R. et al. Diabetologia 1983;25:496
8. Larsson E. L. et al. Int J Immunopharmacol 1987;9:425
9. Carlsten H. et al. APMIS 1989;97:728
10. Kalland T. et al. J Immunol 1985;134:3956
11. Kalland T. J Immunol 1990;144:4472
12. Kalland T. Cancer Res 1986;46:3018
13. Tarkowski A. et al. Immunology 1986;59:589
14. Tarkowski A. et al. Arthrit Rhemat 1986;29:1405
15. Shafrir E. In Rifkin H., Porte D. Jr (eds) Diabetes Mellitus: Theory and practice (4th ed). Amsterdam: Elsevier; chapter 20
16. Nishimura M. et al. In Shafrir E, Renold A. E. (eds) Lessons from Animal Diabetes, II. London: J. Libbey, 1988; pp 165–6
17. Makino S. et al Exp Anim 1986;35:495
18. Ogawa S. et al. Biomed Res 1985;103
19. Mori Y. et al. Diabetologia 1986;29:244
20. Harada M. et al. Exp Anim 1986;35:501
21. Ikehara S. et al. Proc Natl Acad Sci USA 1985;82:7743
22. Bach J. F. et al. In Shafrir E, Renold A. E. (eds) Lessons from Animal Diabetes, II. London: J Libbey, 1988; pp 127–130
23. Miller B. J. et al. J Immunol 1988; 140:52
24. Koike T. et al. Diabetes 1987;36:539
25. Miyagawa J. et al. Diabetologia 1990;33:503

We claim:

1. A method for preventing, treating or ameliorating Type I diabetes, which comprises:

administering an effective amount of an anti-diabetic quinoline-3-carboxamide of formula I, or a pharmaceutically acceptable salt thereof, to a patient in need thereof:

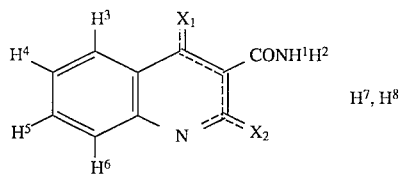

wherein ----- represents two conjugated double bonds between the atoms comprised by the dashed line, $X_1$ and $X_2$ are independently selected from an oxygen atom or $NH^9$, $H^{1-9}$ independently represent a hydrogen atom or a substituent, wherein $H^7$ and $H^8$ are attached to different atoms selected from $X_1$, $X_2$ and the ring nitrogen atom of the quinoline ring, said $X_1$ and $X_2$ being bound by a single bond to the ring when $H^7$ or $H^8$ is bonded thereto and by a double bond when $H^7$ or $H^8$ is not bonded thereto.

2. The method according to claim 1, wherein said patient has Type I diabetes.

3. The method according to claim 1, wherein $H^1$ is a phenyl group and $H^2$ is a methyl group.

4. The method according to claim 3, wherein $H^{3-7}$ are each hydrogen.

5. The method according to claim 1, wherein $X_1$ and $X_2$ are oxygen atoms.

6. The method according to claim 5, wherein $X_1$ is —OH and $X_2$ is =O.

7. The method according to claim 1, wherein the compound is N-phenyl-N-methyl-1,2-dihydro-4-hydroxy-1-methyl-2-oxo-quinoline-3-carboxamide.

8. The method according to claim 1, wherein said administration is by an oral route.

9. A method for treating insulitis, which comprises administering an anti-insulitis effective amount of a quinoline-3-carboxamide compound of formula (I) to a patient in need thereof:

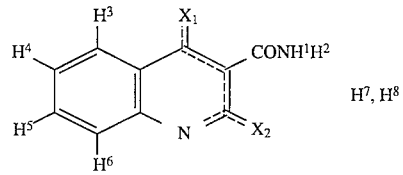

wherein ----- represents two conjugated double bonds between the atoms comprised by the dashed line, $X_1$ and $X_2$ are independently selected from an oxygen atom or $NH^9$, $H^{1-9}$ independently represent a hydrogen atom or a substituent, wherein $H^7$ and $H^8$ are attached to different atoms selected from $X_1$, $X_2$ and the ring nitrogen atom of the quinoline ring, said $X_1$ and $X_2$ being bound by a single bond to the ring when $H^7$ or $H^8$ is bonded thereto and by a double bond when $H^7$ or $H^8$ is not bonded thereto.

* * * * *